(12) United States Patent
Sharpe et al.

(10) Patent No.: US 9,255,874 B2
(45) Date of Patent: Feb. 9, 2016

(54) FLUID STREAM IMAGING APPARATUS

(71) Applicant: CYTONOME/ST, LLC, Boston, MA (US)

(72) Inventors: Johnathan Charles Sharpe, Hamilton (NZ); Donald Francis Perrault, Jr., Brighton, MA (US); Nemanya Sedoglavich, Boston, MA (US)

(73) Assignee: CYTONOME/ST, LLC, Boston, MA (US)

( * ) Notice: Subject to any disclaimer, the term of this patent is extended or adjusted under 35 U.S.C. 154(b) by 0 days.

(21) Appl. No.: 14/190,638

(22) Filed: Feb. 26, 2014

(65) Prior Publication Data

US 2014/0176704 A1  Jun. 26, 2014

Related U.S. Application Data

(63) Continuation of application No. 13/366,124, filed on Feb. 3, 2012, now Pat. No. 8,681,335.

(60) Provisional application No. 61/439,757, filed on Feb. 4, 2011.

(51) Int. Cl.
*G01N 21/59* (2006.01)
*G01N 15/14* (2006.01)

(52) U.S. Cl.
CPC ............ *G01N 15/14* (2013.01); *G01N 15/1404* (2013.01); *G01N 15/1434* (2013.01); *G01N 2015/144* (2013.01); *G01N 2015/1406* (2013.01); *G01N 2015/149* (2013.01)

(58) Field of Classification Search
USPC ......... 356/432–444, 246, 317–318, 399, 410, 356/71–73; 436/63, 8, 18, 23, 164
See application file for complete search history.

(56) References Cited

U.S. PATENT DOCUMENTS

| | | | |
|---|---|---|---|
| 5,916,449 A * | 6/1999 | Ellwart et al. | 210/745 |
| 6,372,506 B1 | 4/2002 | Norton | |
| 6,589,792 B1 | 7/2003 | Malachowski | |
| 6,941,005 B2 * | 9/2005 | Lary et al. | 382/133 |
| 7,586,604 B2 * | 9/2009 | Sharpe et al. | 356/338 |
| 8,358,412 B2 * | 1/2013 | Kanda | 356/337 |
| 8,705,031 B2 * | 4/2014 | Sedoglavich et al. | 356/337 |
| 2001/0033380 A1 * | 10/2001 | Colon | 356/436 |
| 2004/0086159 A1 * | 5/2004 | Lary et al. | 382/128 |
| 2004/0169867 A1 * | 9/2004 | Sharpe | 356/621 |
| 2006/0079000 A1 * | 4/2006 | Floriano et al. | 436/164 |
| 2007/0064034 A1 * | 3/2007 | Hawkins et al. | 347/14 |
| 2007/0195310 A1 | 8/2007 | Kanda | |
| 2008/0259342 A1 * | 10/2008 | van den Engh et al. | 356/445 |
| 2010/0049119 A1 * | 2/2010 | Norman et al. | 604/31 |
| 2010/0297759 A1 | 11/2010 | Kanda | |
| 2013/0258075 A1 * | 10/2013 | Muraki et al. | 348/61 |

FOREIGN PATENT DOCUMENTS

EP   1947442 A2   7/2008

OTHER PUBLICATIONS

PCT International Search Report and Written Opinion dated Mar. 15, 2012 issued in related PCT Application No. PCT/US2012/023843 (11 pages).

* cited by examiner

*Primary Examiner* — Sang Nguyen
(74) *Attorney, Agent, or Firm* — McCarter & English, LLP; David R. Burns

(57) ABSTRACT

A fluid stream imaging apparatus having either optics for manipulating the aspect ratio or sensing elements configured for manipulating the aspect ratio of an image of the fluid stream. This application may also relate to a system for acquiring images of a portion of a fluid stream at high speeds for image processing to measure and predict droplet delays for individual forming particles.

9 Claims, 5 Drawing Sheets

FLUID STREAM IMAGING APPARATUS

This application is a continuation of and claims the benefit of priority to U.S. Ser. No. 13/366,124, filed on Feb. 3, 2012 which claims the benefit of priority to U.S. Provisional Patent Application Ser. No. 61/439,757, filed on Feb. 4, 2011, the contents of each application are herein incorporated by reference in their entirety.

FIELD

The present disclosure generally relates to the field of flow cytometry, and more particularly a fluid stream imaging apparatus.

BACKGROUND

Various flow cytometers and microfluidic systems exist for the purpose of analyzing and sorting particles. Each of these instruments has various shortcomings relating to their ability to maintain accurate sort actions. Jet-in-air flow cytometers are commonly used for the purpose of sorting particles based on detected characteristics. The operation of a jet-in-air flow cytometer may involve producing a coaxial fluid stream in a nozzle. The coaxial fluid stream has a core stream of sample, which includes the particles or interest, and an outer stream of sheath fluid. The sheath fluid provides a means for positioning particles and preventing clogging in the nozzle, as well as, for providing conductive medium suitable for retaining an applied charge.

The coaxial fluid stream may be perturbed with an oscillator, such as a piezoelectric crystal, resulting in the formation of droplets downstream of a nozzle. The droplets may contain individual particles or a small group of particles. Based on a desired sort action, each droplet may be charged just prior to separating from the fluid stream at a break off point. The appropriate time for applying this charge is known as the drop delay. As droplets may be formed at a rate of between about 20,000 per second and 200,000 per second, the drop delay must be very precisely calculated.

Historically, the drop delay was determined through an iterative series of protocols largely consisting of trial and error test streams having varying drop delays. Beads or particles were run through test streams and collected in puddles. The number of beads or particles collected in each puddle provided an indication of the drop delay. Such manual protocols are time intensive and may be lacking in the precision required to achieve extremely accurate sort decisions and are incapable of real time verifications or adjustments.

U.S. Pat. No. 6,248,590 describes an attempt to monitor the drop delay with the use of a single camera for imaging a portion of the fluid stream, or with multiple cameras for imaging separate portions of the fluid stream, such as for determining the speed of particles at the nozzle and at the speed of particles at a drop off point. From this information an approximation is derived utilizing an exponential decay model. However, the formation of droplets may not be so easily predictable and because only a portion of the stream is monitored, upstream changes may not be detected reliably.

U.S. Patent application publication 2001/02218892 provides a camera mounted on a movable stage for taking multiple images of a fluid stream. The images are then stitched together and the widths are determined. From this information a number of droplets, peaks, and periods between the inspection zone and the drop delay maybe determined. This configuration provides for means of producing a composite image of the entire fluid stream, but is lacking the ability to monitor the fluid stream in real time because the camera must traverse the fluid stream at a rate thousands of times slower than the fluid stream itself. Further, a stitched together image may not accurately reflect the stream at any particular time and is time consuming to produce. Changes in operating conditions, such as oscillator frequency, oscillator amplitude, temperature, surface tension, and harmonic conditions may vary the stream during the time in which the individual images are being captured. Positional changes in the excitation source or the droplet break off point during operation, upon start up, or during other changes cannot quickly be realized by the described system because a series of images must first be captured and then stitched together.

SUMMARY OF INVENTION

Certain aspects of this disclosure relate to an improved system for imaging a fluid stream, such as in a flow cytometer for analyzing and/or sorting particles. The provisions of such a system, in one embodiment include: a fluid delivery system having a nozzle for producing a fluid stream, the fluid delivery system having an oscillator for perturbing the fluid stream into droplets at a break off point downstream of the nozzle; an excitation energy source for interrogating the fluid stream at an inspection zone; an optical system for manipulating the aspect ratio of an image of the fluid stream; and a sensing element for sensing the manipulated image of the fluid stream. Such a system may be capable of producing an image of a fluid stream with sufficient detail along the flow axis of the stream and across the flow axis of the stream for deriving an accurate break off point and an accurate drop delay.

Other aspects of this disclosure relate to an improved imaging device for a fluid stream, such as in a flow cytometer for analyzing and sorting particles. The provisions of such a system, in one embodiment include: a fluid delivery system having a nozzle for producing a fluid stream, the fluid delivery system having an oscillator for perturbing the fluid stream into droplet at a break off point downstream of the nozzle; an excitation energy source for interrogating the fluid stream at an inspection zone; an optical system for producing a image of the fluid stream, the image of the fluid stream including at least the inspection zone and the break off point; and a high resolution sensing element for sensing an image of the fluid stream.

Still other aspects of this disclosure may relate to a system of processing digital images in real time to predict the drop delay of each forming droplet. Such a system may include: a fluid delivery system having a nozzle for producing a fluid stream, the fluid delivery system having an oscillator for perturbing the fluid stream into droplet at a break off point downstream of the nozzle; an excitation energy source for interrogating the fluid stream at an inspection zone; a detector for detecting electromagnetic radiation from particles at the inspection zone and for determining particle characteristics; a controller for charging the fluid stream based on the detected particle characteristics; an optical system for producing a image of the fluid stream, the image of the fluid stream including at least the break off point, wherein the optical system takes multiple images per droplet; a sensing element for sensing a plurality of images of the fluid stream; and a processor for processing the detected image of the fluid stream, wherein the processor includes is responsive to images of the fluid stream to determine and/or predict the time at which a droplet breaks off the fluid stream.

One broad object provided in this disclosure can be a camera to produce a single image of a fluid stream, where that image includes both an interrogation point, or inspection zone, and the break off point, and where the necks of forming droplets are captured with sufficient resolution across the flow axis (stream width) for precisely determining or updating a drop delay. From this image changes in the distance from the inspection zone to the break off point may provide more accurate drop delay information than previous systems.

An object of this disclosure can be to provide an apparatus and method for performing more accurate sort actions by precisely monitoring the fluid stream. Specifically, one broad object of the apparatus provided herein is to provide the capability for manipulating an image of the entire fluid stream into a format allowing important features throughout the entire fluid stream to be monitored in real time.

Another broad object provided herein may be to image the entire fluid stream, or part of the fluid stream, and to provide sufficient resolution to monitor droplets forming in real time, so that a specific drop delay can be determined, or predicted, for each sorted droplet. Images may be processed digitally to determine changes in the drop delay or other parameters such as the location of the break off point or location of the inspection zone.

A broad object of this disclosure can be to provide an apparatus for sorting particles and a method of sorting particles which meets the needs described above. Naturally, further objects of the disclosure are provided throughout the specification.

MODES FOR CARRYING OUT THE INVENTION

The embodiments described herein relate to the analysis and sorting of particles, such as by flow cytometry. A number of inventive concepts provided below may be combined or applied to sorting systems other than flow cytometers.

Figure 1:
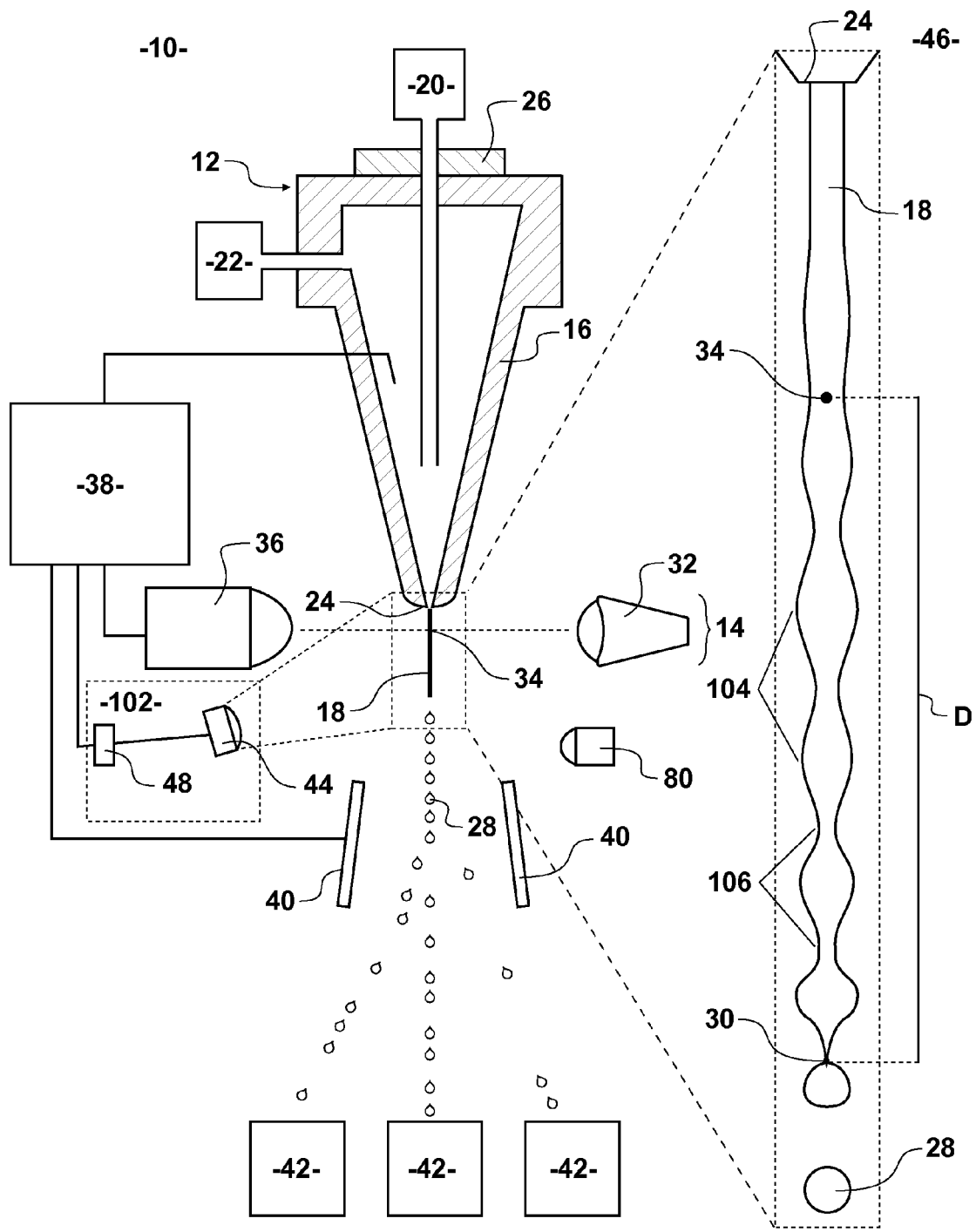
FIG. 1 illustrates a flow cytometer with a fluid stream imaging apparatus in accordance with certain embodiments described herein.

Now referring primarily to FIG. 1, an example of a flow cytometer 10 is illustrated as a jet-in-air flow cytometer. The flow cytometer 10 may include a fluid delivery system 12, such as a nozzle 16 having a nozzle orifice 24 for delivering a fluid stream 18 to a detection system 14. The fluid stream 18 may be perturbed into droplets 28 by an oscillator 26. The droplets 28 may pass through an electromagnetic field produced by deflection plates 40. A charge applied to each droplet 28 will define a path into one of one or more collection containers 42.

The fluid stream 18 may comprise a coaxial fluid steam having an inner core stream of sample 20 and an outer stream of sheath fluid 22. The fluid stream 18 may exit the nozzle orifice 24 with increasingly pronounced undulations 104 or decreasing neck 106 thicknesses in a downstream direction until a break off point 30 is reached where droplets 28 break away from the fluid stream 18. The break off point 30 is illustrated as the last point at which a droplet 28 contacts the fluid stream 18. In the field of flow cytometry, this location represents the last point in time a charge may be applied to a droplet 28.

The detection system 14 may include an excitation energy source 32 for providing energy, such as a laser, a light emitting diode, or an arc lamp, to the fluid stream 18 and particles of interest contained in the sample 20. The excitation energy source 32 is aligned with an inspection zone 34 on the fluid stream 18 for interrogating particles as they pass the inspection zone 34. The inspection zone 34 may be located downstream of the nozzle orifice 24 or may be located within a cuvette or a flow chamber upstream of the nozzle orifice 24. Reflected or emitted electromagnetic radiations from the fluid stream 18 and particles in the fluid stream 18 can be collected by a detector 36. The detector 36 may include any number of detectors configured in the forward, side, or back direction relative to the excitation energy source 32. Various optics, such as filters, mirrors, dichoric mirrors, splitters, and other reflective and refractive elements, may be used to detect electromagnetic radiation at any number of wavelengths and/or in any number of directions and in a variety of combinations.

Detected signals may be processed for the classification of particles within the fluid stream 18 and sort decisions may be made at a controller 38. The controller 38 may include acquisition and sort electronics in the form of analog or digital components for processing signals from the detector and applying a sort logic. Once a sort decision is made, the controller 38, may act to charge the fluid stream 18 through the sample 22 at in the nozzle 16 so that the droplets 28 are deflected by deflection plates 40 into the appropriate container 42.

The timing at which the appropriate charge is applied to the fluid stream 18 must be closely matched to the time a particle is in a droplet at the break off point 30 in order to ensure an accurate sort action. An imaging device 102 may be provided to monitor or update the distance between the break off point 30 and the inspection zone 34 and the number of undulations 104 in the fluid stream 18 to predict a current or updated drop delay. The imaging device 102 may include an optical system 44 and a sensing element 48 for capturing an image of the fluid stream 46 for the purpose of modifying or detecting the appropriate drop delay for accurate sort decisions.

A strobe 80 may illuminate the fluid stream 18 at predicted intervals to create an image of the fluid stream 46 as photons reflected from the object of the fluid stream 18. With reference to the figures, the fluid stream, otherwise known as the object, is indicated as character reference 18, while an image of the fluid stream within a field of view is indicated as character reference 46. When character references 18 and 46 are directed to the same portion of a figure, character reference 18 should be understood to represent the object of the fluid stream, while character references 46 should be understood to represent the image of the fluid stream as it would be captured or sampled by the optic system 44. The optical system 44 may include a series of optical elements for manipulating the image of the fluid stream 46. As one example, the optical system 44 may comprise multiple lenses or multiple mirrors, other reflective or refractive elements, and combinations of different reflective and refractive elements. In one embodiment, the optical system 44 may manipulate the aspect ratio of the image of the fluid stream 46, such as compressing the length 68 (seen in FIG. 2) of the fluid stream and expanding the width 70 (seen in FIG. 2) of the fluid stream. By manipulating the aspect ratio to form a manipulated image of the fluid stream 50, the optical system 44 may serve to preserve relevant information pertaining to the drop delay. As one non-limiting example, the length 68 (along the flow axis) of the image of the fluid stream 46 may be compressed by a factor of about 2 times (or magnified by a factor of 0.5). Such a compression may allow for the entire length of the fluid stream 18 to be captured in an image with sufficient resolution to identify and digitally process undulations 104 and necks 106 in the fluid stream 18. At the same time, the width 70 (across the flow axis) may be magnified by a factor of 5 in order to amplify features such as the thickness of the necks 106 in the fluid stream 18. Such an optical system 44 for modifying an image of a fluid stream 46 could provide, in a single image, enough information to determine or modify drop delays.

The sensing element 48 may be any sensing element 48 capable of converting an image into a series of electrical or digital signals. As one example, the sensing element 48 may be a charge coupled device (CCD). A charge coupled device may operate to produce a series of analog pulses based upon the light intensity received at each pixel of the CCD. These pulses may then be digitized to produce a digital image. Similarly, a complementary metal-oxide-semiconductor (CMOS) may be used for detecting pulses at individual pixels. Other sensors and configurations for detecting the light intensity of an image in high resolution may also be used, such as a photodiode array or a sensor array.

Figure 2:
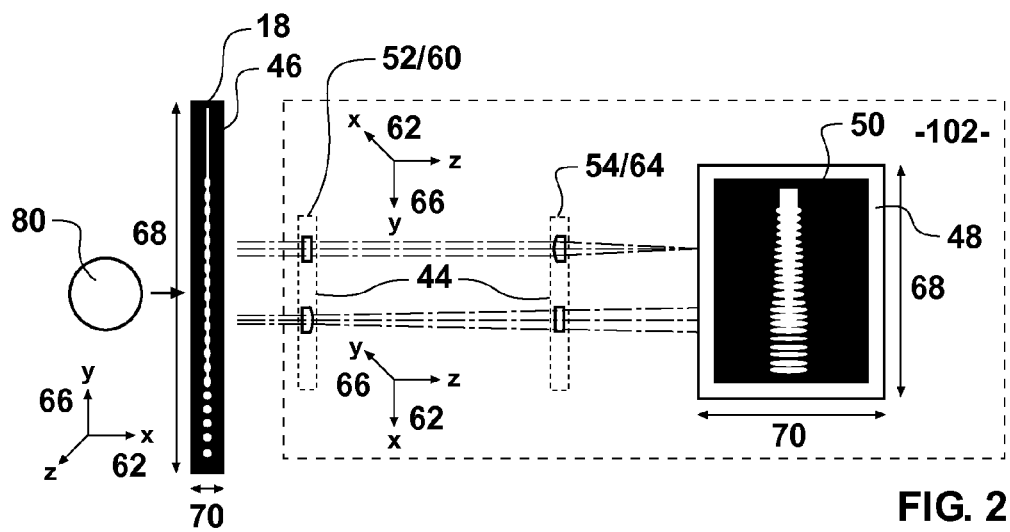
FIG. 2 illustrates an embodiment of a fluid stream imaging apparatus in accordance with certain embodiments described herein.

Turning to FIG. 2, an imaging device 102 is illustrated which may be used for imaging a fluid stream 18 of a flow cytometer 10. An illumination source, such as a strobe 80, laser, lamp, or LED strobe, may illuminate the fluid stream 18 periodically, or on demand, to ensure an image of the fluid stream 46 is produced. The image of the stream 46 may be manipulated through an optical system 44 comprising a first optical element 52 and a second optical element 54 for producing a manipulated image of the fluid stream 50 incident upon the sensing element 48. Each of the first optical element 52 and the second optical element 54 may be refractive optical elements, reflective optical elements, or diffractive elements. FIG. 2 illustrates the first optical element 52 as a first cylindrical lens 60 for manipulating the image of the stream 46 in a first axis 62. Relative to the image of the fluid stream 46 depicted in FIG. 2, the first axis 62 may be referred to as the X-axis. Throughout the following description the first axis 62 will correspond to the width 70 of the fluid stream 18, but the designation as the X-axis may be considered arbitrary. The manipulated image of the fluid stream 50 may retain its dimension in a second axis 66, such as the Y-axis, which is orthogonal to the first axis 62, after passing through the first cylindrical lens 60. FIG. 2 illustrates the first cylindrical lens in two different planes, and the different effect the first cylindrical lens 60 has on light in each plane is illustrated, as described above. As one example, the first cylindrical lens 60 may be a 25 mm cylindrical lens, such as one available from OptoSigma, part number 022-0160. The first cylindrical lens 60 may magnify the width 70 of the image of the fluid stream 46 by between 3 times and 20 times, or more.

The second optical element 54 may comprise a second cylindrical lens 64 for manipulating the dimensions of the image of the fluid stream 46 in a second axis 66. The second cylindrical lens 64 is illustrated in two different planes as substantially aligned with first cylindrical lens 60 and the combined effect is illustrated in the direction of the manipulated image of the fluid stream 50 in both planes. As a non-limiting example, the second cylindrical lens 64 may reduce the length 68 of the image of the fluid stream 46 in the second axis 66, without further changing the width 70 of the image of the fluid stream 46 in the first axis 62. As one example, the second cylindrical lens 64 may be a 40 mm lens, such as one available from OptoSigma, part number 022-0290. The second cylindrical lens 64 may magnify the stream length 68 by magnitude of between 0.75 and 0.125. The second cylindrical lens 64 may be seen as compressing the length 68 of the image of the fluid stream 46 by a factor between ¼ and 10.

The cylindrical lenses may cooperate to manipulate the aspect ratio of the image of the fluid stream 46 to a ratio of about 10 to 1. Various combinations of magnifications may be used to achieve this ratio, or other ratios. As one non-limiting example, the length 68 of the image of the fluid stream 46 may be magnified by a factor of 0.5 and the width 70 of the image of the fluid stream 46 may be magnified by a factor of 5. Other configurations are contemplated herein, such those for providing aspect ratios of 2 to 1, 4 to 1, 10 to 1, 15 to 1, 20 to 1 or even higher. The optical elements may be placed in any order.

Figure 3:
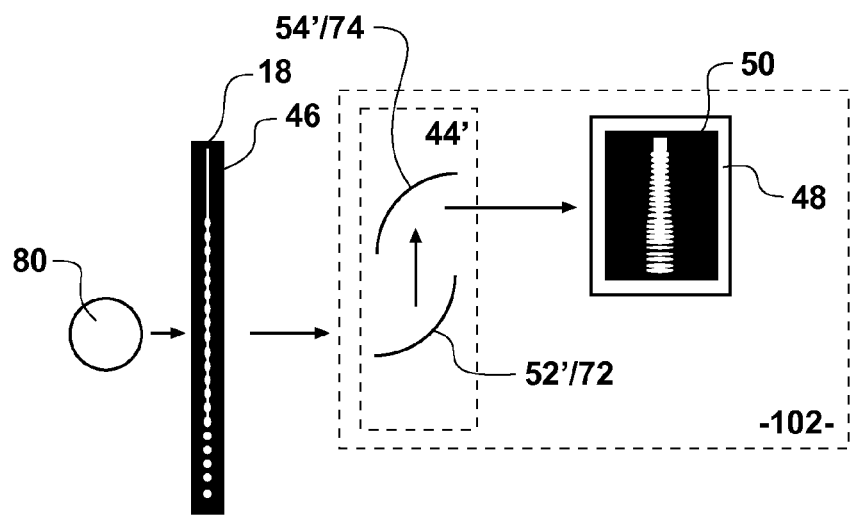
FIG. 3 illustrates an embodiment of a fluid stream imaging apparatus in accordance with certain embodiments described herein.

Referring now to FIG. 3, an imaging device 102 is illustrated having optics system 44' with a first optical element 52' in the form of a first reflective element 72 and a second optical element 54' in the form of a second reflective element 74. The reflective elements may comprise mirrors and particularly mirrors for manipulating the aspect ratio of the images of the fluid stream 46. The first reflective element 72 may comprise a mirror for expanding the width 70 of the image of the fluid stream 46 in a manner similar to that described with respect to FIG. 1. The second reflective element may comprise a mirror for reducing the length 68 of the image of the fluid stream 46 in a manner similar to that described with respect to FIG. 1. It should be appreciated with respect to the reflective and the refractive elements that the first optical element may be either for manipulating the length 70 of the image of the fluid stream 46 or the width 68 of the image of the fluid stream 46. Further, embodiments contemplated herein include combinations of refractive elements and reflective elements, such as, one or more cylindrical lenses for modifying one dimension of the image of the fluid stream and one or more mirrors for modifying another dimension of the image of the fluid stream 46.

In still another embodiment, diffractive elements may be used for manipulating the aspect ratio of the image of the fluid stream 46. It should be understood that other optics for manipulating the aspect ratio of the image of the fluid stream 46 may be used in conjunction the optics system 44 to deliver the image of the fluid stream 46 to the optical system 44 or to the sensing element 48.

Figure 4:
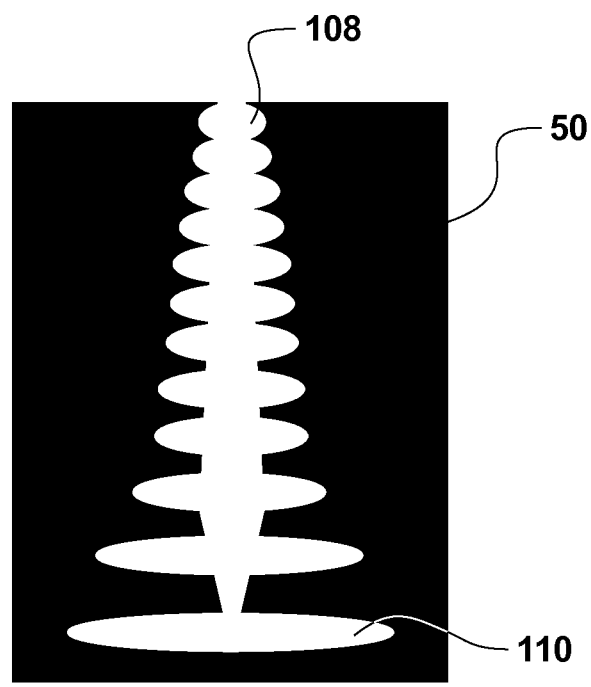
FIG. 4 illustrates a manipulated image of a fluid stream with a continuous change in the aspect ratio along the flow axis.

Combinations of optical elements may be used to modify the aspect ratios of the manipulated image of the fluid stream 50 differently at different points along the length 68 of the fluid stream 18. FIG. 4 illustrates a manipulated image of the fluid stream 50 produced by an optical system 44 configured for continuous gradient. A first aspect ratio 108 at the top of the manipulated image of the fluid stream 50, may remain 1 to 1, while the a second aspect ratio 110 near the break off point 30, may be 5 to 1, 10 to 1, or another ratio. Resolving the width of the fluid stream 18 near a break off point well, may increase the accuracy of detecting the break off point 30 and changes in the break off point 30. A continuous gradient may be created with a combination of lenses and mirrors as well as with one or more gradient index GRIN lenses.

Figure 5:
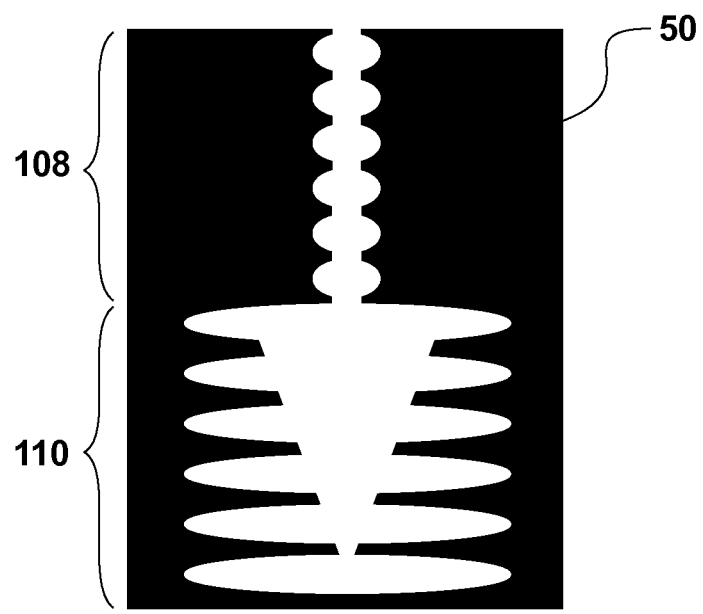
FIG. 5 illustrates a manipulated image of a fluid stream with a single disjointed change in the aspect ratio along the flow axis.

FIG. 5 illustrates a disjointed image, whereby a first portion of the manipulated image of the fluid stream 50 is transmitted at a first aspect ratio 108, such as 1 to 1, and a second portion of the manipulated image of the fluid stream 50 is transmitted at a second aspect ratio 110, such as 5 to 1 or 10 to 1. It should be appreciated; the disjointed image may be a compilation of multiple images having different aspect ratios, such as 3, 4, 5, 8, 10 or more images having different aspect ratios.

Each of the images created by the optics of FIG. 2 or FIG. 3 may be transmitted onto a single sensing element with or without magnification. Alternatively, the manipulated image of the fluid stream 50 may be projected onto multiple sensing elements or a high resolution sensing element described in more detail below.

Figure 6:
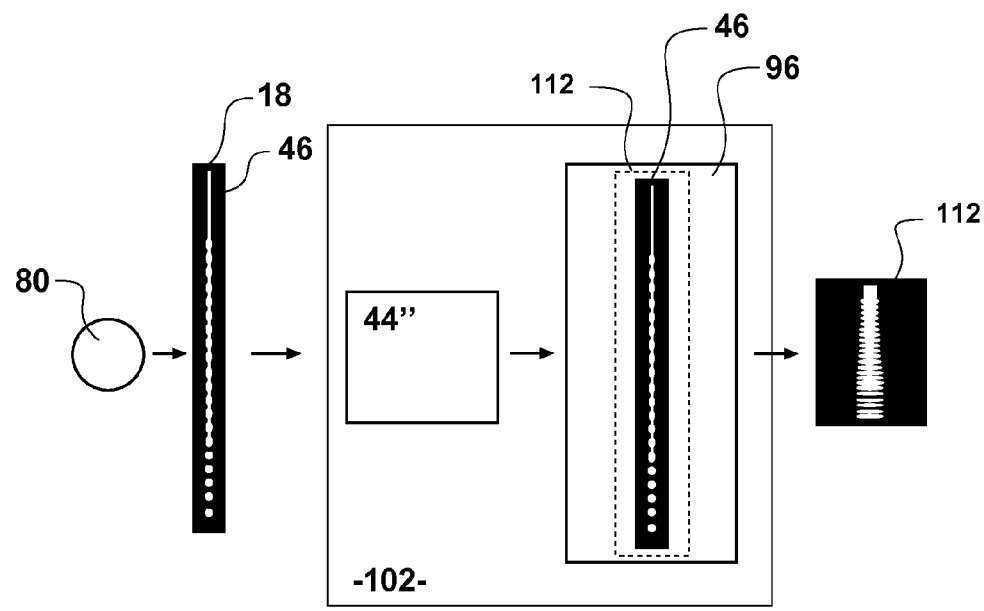
FIG. 6 illustrates an embodiment of a fluid stream imaging apparatus in accordance with certain embodiments described herein.

Referring to FIG. 6, an imaging device 102 is illustrated with an optical system 44" which does not manipulate the aspect ratio of the image of the fluid stream 46. Instead, the optic system 44" may provide for a zoom factor of 10 for projecting an image of the fluid stream 46 onto a high resolution sensing element 96. The high resolution sensing element 96 may comprise a high resolution CCD, such as one having between 0.3 megapixels and 20 megapixels or more. By way of non-limiting examples the CCD may have 10 megapixels or 20 megapixels. The image of the fluid stream 46 may then be manipulated at the level of the high resolution sensing element 96 through a cropping function. The cropped high resolution image 104 may provide a manipulated aspect ratio similar to those manipulated with the optics systems 44 previously described.

Figure 7:
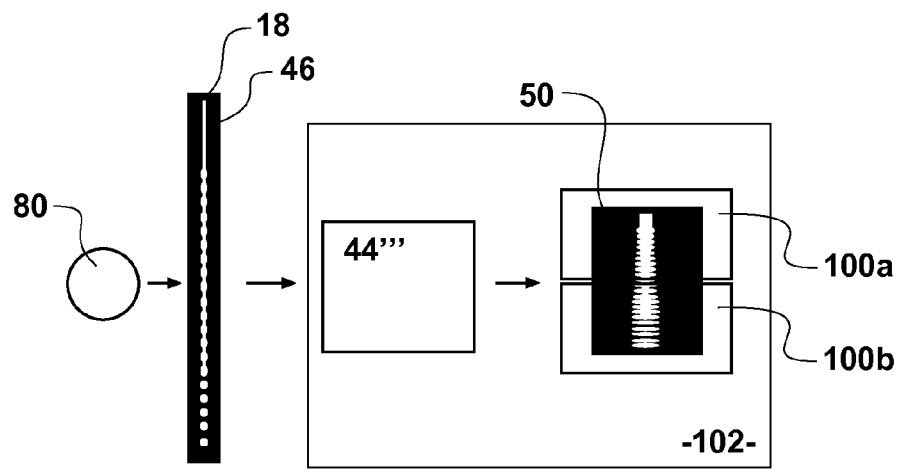
FIG. 7 illustrates an embodiment of a fluid stream imaging apparatus in accordance with certain embodiments described herein.

Referring now to FIG. 7 an imaging device 102 is illustrated with a single optical system 44''' and two or more spatially separated sensing elements 100a, 100b. The single optics system 44''' may manipulate the aspect ratio of the image of the fluid stream 46, or may maintain a 1 to 1 aspect ratio with respect to the fluid steam length 68 and width 70. The single optics system 44''' may also provide magnification, or may merely focus the image of the fluid stream 46. FIG. 7 illustrates the image of the fluid stream 46 with a manipulated aspect ratio, but the images may also be magnified, or some combination thereof.

It may be of particular interest in a system having multiple sensing elements 100 to ensure the most important regions of interest fall on the sensing elements 100 and not in any gap created by spacing. For example, it may be desirable to ensure the inspection zone 34 is well captured on one sensing element and that the break off point 30 is well captured on another sensing element. This may help to ensure the break off point 30 is accurately measured and the distance D between the inspection zone 34 and the break off point 30 is accurately determined. In one embodiment, the sensing element 100 corresponding to the break off point 30 may operate at an improved resolution compared to the other sensing elements. In another embodiment, the portion of the image with the droplet break off 30 may be capture on a separate camera or sensing element. Other optical configurations where portions of the image may be split to multiple sensing elements that have an overlapping field of view within the object plane may also be employed where, when processed, or recombined, there are no discontinuities in the image.

Figure 8:
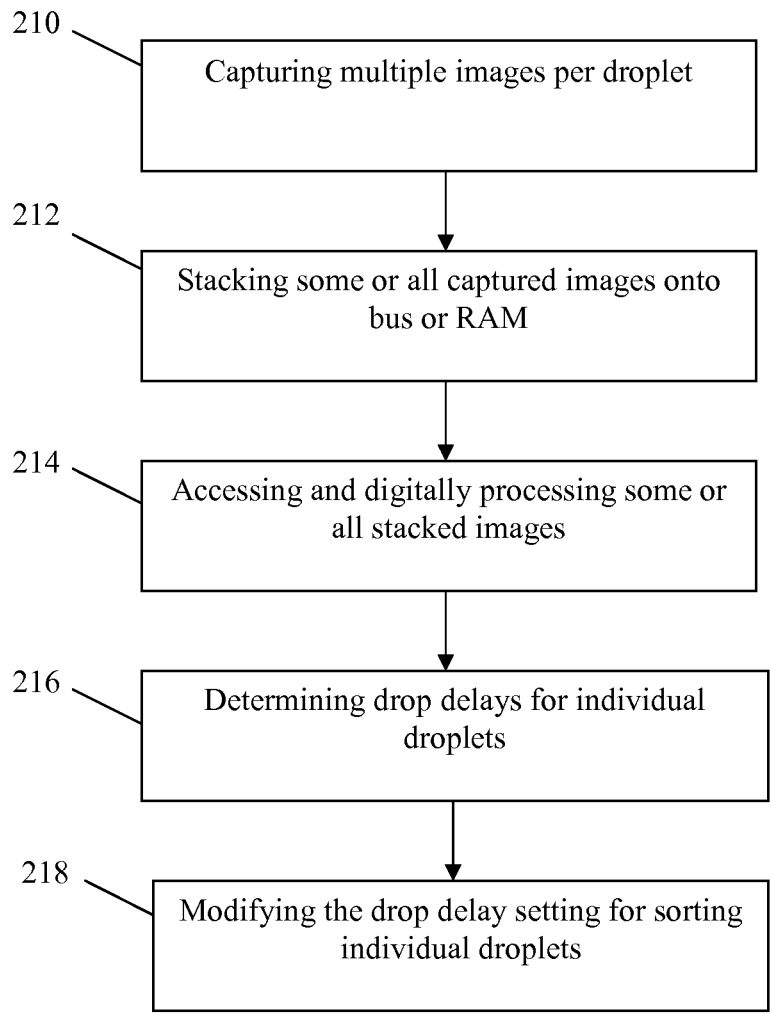
FIG. 8 illustrates a flow chart of a method in accordance with certain embodiments described herein.

FIG. 8 depicts an embodiment of a method where a high resolution sensing element 96 may be used in conjunction with high speed data acquisition and processor in order to take multiple images of a forming droplet and to determine the precise time at which each droplet breaks way from the steam, as shown in step 210. Such high speed computations may be made on the central processing unit of a computer, on a single digital signal processor or on a field programmable gate array. Any of these processors may be programmed to modify the calculated drop delay based on digital processing of one or more images.

The high resolution sensing element 96 may form a portion of a high speed, high resolution camera which may be used in conjunction with a flow cytometer 10, like the one depicted in FIG. 1. The microprocessor may be located in the controller 38 or elsewhere, and may be in communication with the high resolution sensing element 96 for extracting features from the high resolution image and making determinations as to the time at which the next droplet will break away from the fluid stream. High repetition rate or on-demand images may be captured and transferred at a sufficiently high rate into memory or other suitable storage mechanisms for real time processing, as illustrated in step 212. At step 214, data processing algorithms may be used to extract certain features such as the thickness of the droplets or the width of the neck which may provide valuable information regarding the time at which droplet will break from the fluid stream. As a non-limiting example, a certain region of interest may be processed to track the position of the last neck of last attached drop. Multiple images may be acquired and processed per droplet formation cycle so that the droplet formation progress can be tracked and estimated, particularly the drop delay, as illustrated at step 216. Finally, with sufficient resolution, at step 218 the processor may modify the drop delay on a droplet-by-droplet basis as a function of processing the plurality of images to determine the point at which an individual droplet is about to break free from the continuous fluid stream. These measurements may be particularly useful when increased chaotic behavior is observed as particles are flowing within the fluid stream. It may not be necessary to observe the actual droplet formation, or wait for actual droplet to form, since certain latency exists within electronic circuitry. In fact, one may engage the charge circuitry early to ensure that a suitable voltage level will be applied to the continuous fluid stream prior to the droplet formation event. The processor may then modify the existing predicted drop delay, or the calibrated or average drop delay, based upon this information. A predictive model may also be generated from these observations.

Similarly, the processor may modify the drop delay on a droplet-by-droplet basis as a function of processing the plurality of images to determine the point at which the fluid stream between two forming droplets becomes disconnected.

The high speed camera may take pictures as rapidly as between every microsecond and every 50 microseconds. In one embodiment, the high speed camera can operate in two modes: a coarse mode and a fine mode. The coarse mode may apply when a droplet has just finished forming and the fine mode may apply when a droplet is approaching the break off point. The high speed camera may operate to take, or process, images more rapidly in fine mode than in coarse mode. The high speed camera may operate in phase or out of phase with the droplet formation signal or with a particular phase offset.

The processor may include an image processing algorithm in the form of written executable computer instructions for determining the time at which the next droplet will break off the fluid stream. The image processing algorithm may be in the form of instructions stored on a digital signal processor, or a bitmap look up table on a field programmable gate array. The algorithm may define the periods for coarse mode and fine mode, whereby based upon the features extracted from the images, the algorithm determines the rate at which images should be captured. Images may be captured at two discrete rates or there may be a continuous transfer between two or more rates. The algorithm may selectively utilize individual images from a plurality of image captured events.

Features extracted from the images of the fluid stream 46 may include: edge detection, fluid stream features, droplet shape and position, neck geometry and position, aspect ratio, contrast, statistical characteristics such as means and standard deviation any parameter, and other features which may be extracted from the images.

As can be easily understood from the foregoing, the basic concepts of the present invention may be embodied in a variety of ways. The invention involves numerous and varied embodiments of flow cytometry acquisition and sort electronics and methods including, but not limited to, the best mode of the invention.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "sensing element" should be understood to encompass disclosure of the act of "sensing"—whether explicitly discussed or not—and, conversely, were there effectively disclosure of the act of "sensing", such a disclosure should be understood to encompass disclosure of a "sensing element" and even a "means for sensing." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity; for example, "a container" refers to one or more of the containers. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

Thus, the applicant(s) should be understood to claim at least: i) a fluid stream imaging device for modifying the aspect ratio of an image of a fluid, ii) an fluid stream imaging device with a high resolution sensing element, iii) a flow cytometer with an optical system for imaging droplet formation and processing those images to determine droplet break off times, iv) the related methods disclosed and described, v) similar, equivalent, and even implicit variations of each of these devices and methods, vi) those alternative embodiments which accomplish each of the functions shown, disclosed, or described, vii) those alternative designs and methods which accomplish each of the functions shown as are implicit to accomplish that which is disclosed and described, viii) each feature, component, and step shown as separate and independent inventions, ix) the applications enhanced by the various systems or components disclosed, x) the resulting products produced by such systems or components, xi) methods and apparatuses substantially as described hereinbefore and with reference to any of the accompanying examples, and xii) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A flow cytometer comprising:
   a. a fluid delivery system having a nozzle for producing a fluid stream, the fluid delivery system having an oscillator for perturbing the fluid stream into droplets at a break off point downstream of the nozzle;
b. an excitation energy source for interrogating the fluid stream at an inspection zone;
c. an optical system for producing an image of the fluid stream, the image of the fluid stream including at least the inspection zone and the break off point; and
d. a sensing element for sensing the image of the fluid stream,
   wherein a distance between an interrogation point within the inspection zone and the break off point is determined from the image of the fluid stream produced by the optical system.

2. The flow cytometer of claim 1, wherein the sensing element is a high resolution sensing element having a resolution between 3 megapixels and 20 megapixels.

3. The flow cytometer of claim 1, wherein the aspect ratio of the image of the fluid stream sensed by the sensing element is manipulated.

4. The flow cytometer of claim 1, wherein the sensing element comprises a single high resolution CCD sensor for sensing the image of the fluid stream.

5. The flow cytometer of claim 1, wherein the sensing element comprises a single high resolution CMOS sensor for sensing the image of the fluid stream.

6. The flow cytometer of claim 1, wherein the sensing element comprises at least at least two spaced apart sensing elements each for sensing a portion of the image of the fluid stream produced by the optical system.

7. A flow cytometer comprising:
a. a fluid delivery system having a nozzle for producing a fluid stream, the fluid delivery system having an oscillator for perturbing the fluid stream into droplets at a break off point downstream of the nozzle;
b. an excitation energy source for interrogating the fluid stream at an inspection zone;
c. an optical system for producing an image of the fluid stream, the image of the fluid stream including at least the inspection zone and the break off point; and
d. a sensing element for sensing the image of the fluid stream,
   wherein the number of undulations in the stream between an interrogation point within the inspection zone and the break off point is determined from the image of the fluid stream produced by the optical system.

8. The flow cytometer of claim 7, further comprising:
a processor configured with an image processing algorithm,
wherein the algorithm comprises a coarse determination and a fine determination, and
wherein the image processing algorithm selects one of the following features from the plurality of images to determine the time when a droplet will break off the fluid stream: edge detection, fluid stream features, droplet shape, aspect ratio, contrast, and combinations thereof.

9. The flow cytometer of claim 7, further comprising:
a controller configured to apply a drop delay when charging the fluid stream for separating particles; and
a processor configured to update the drop delay on a droplet-by-droplet basis.

* * * * *